US012396668B2

(12) United States Patent
De Pelsemaeker et al.

(10) Patent No.: US 12,396,668 B2
(45) Date of Patent: Aug. 26, 2025

(54) INTERACTIVE SYSTEM AND ASSOCIATED INTERACTION METHOD

(71) Applicant: Valeo Systemes Thermiques, Le Mesnil Saint-Denis (FR)

(72) Inventors: Georges De Pelsemaeker, Le Mesnil Saint-Denis (FR); Antoine Boilevin, Le Mesnil Saint-Denis (FR)

(73) Assignee: Valeo Systemes Thermiques, Le Mesnil Saint-Denis (FR)

( * ) Notice: Subject to any disclaimer, the term of this patent is extended or adjusted under 35 U.S.C. 154(b) by 383 days.

(21) Appl. No.: 17/782,820

(22) PCT Filed: Nov. 23, 2020

(86) PCT No.: PCT/FR2020/052151
§ 371 (c)(1),
(2) Date: Jun. 6, 2022

(87) PCT Pub. No.: WO2021/111057
PCT Pub. Date: Jun. 10, 2021

(65) Prior Publication Data
US 2023/0011113 A1  Jan. 12, 2023

(30) Foreign Application Priority Data
Dec. 6, 2019 (FR) ...................................... 1913857

(51) Int. Cl.
*A61B 5/16* (2006.01)
*B60W 40/08* (2012.01)

(52) U.S. Cl.
CPC ............. *A61B 5/165* (2013.01); *B60W 40/08* (2013.01); *B60W 2040/0872* (2013.01)

(58) Field of Classification Search
CPC .................. A61B 5/165; B60W 40/08; B60W 2040/0872; B60W 2040/0818;
(Continued)

(56) References Cited

U.S. PATENT DOCUMENTS

2018/0173230 A1* 6/2018 Goldman-Shenhar ...................... B60W 50/08
2019/0008437 A1 1/2019 Ben-Ezra et al.

FOREIGN PATENT DOCUMENTS

WO WO-2018074224 * 4/2018
WO 2019/086856 A1 5/2019
WO WO-2019086856 * 5/2019

OTHER PUBLICATIONS

International Search Report and Written Opinion in corresponding International Application No. PCT/FR2020/052151, mailed Jan. 14, 2021 (12 pages).

(Continued)

*Primary Examiner* — Muhammad Shafi
(74) *Attorney, Agent, or Firm* — Osha Bergman Watanabe & Burton LLP

(57) ABSTRACT

The invention relates to an interactive system (1) with a user (U) occupying a motor vehicle (100) comprising an interface (3) and an operating system for executing an application. According to the invention, the interactive system (1) comprises a measuring device (5) comprising at least one sensor that is configured to acquire at least one physiological parameter of the user (U), and an embedded processing unit (7). The processing unit (7) comprises an interpretation module that is configured to receive the physiological parameter and to define, on the basis of the physiological parameter, a datum representative of the physiological or emotional state of the user (U), and an analysis module that is configured to compare data representative of the physiological or emotional state of the user (U) before and during the execution of an application for managing a remediation exercise, and to adjust at least one parameter of the remediation exercise according to the results of the comparison. The invention also relates to an interaction method implemented at least partly by such an interactive system.

9 Claims, 4 Drawing Sheets

(58) Field of Classification Search
CPC ............. B60W 50/14; B60W 2050/143; G06F 16/337; B60K 28/02
USPC .......................................................... 701/23
See application file for complete search history.

(56) References Cited

OTHER PUBLICATIONS

Office Action in corresponding Chinese Application No. 202080095798.6, dated Mar. 28, 2025 (23 pages).

* cited by examiner

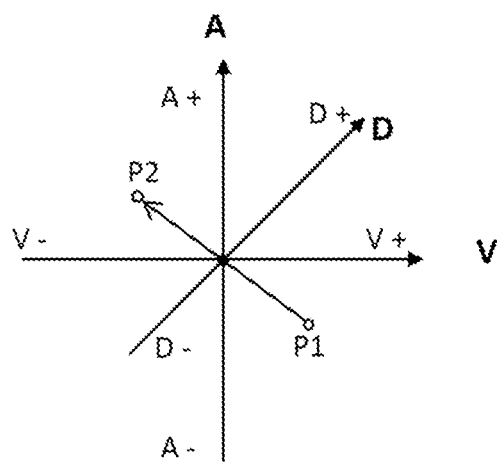
Fig. 4
Fig. 5
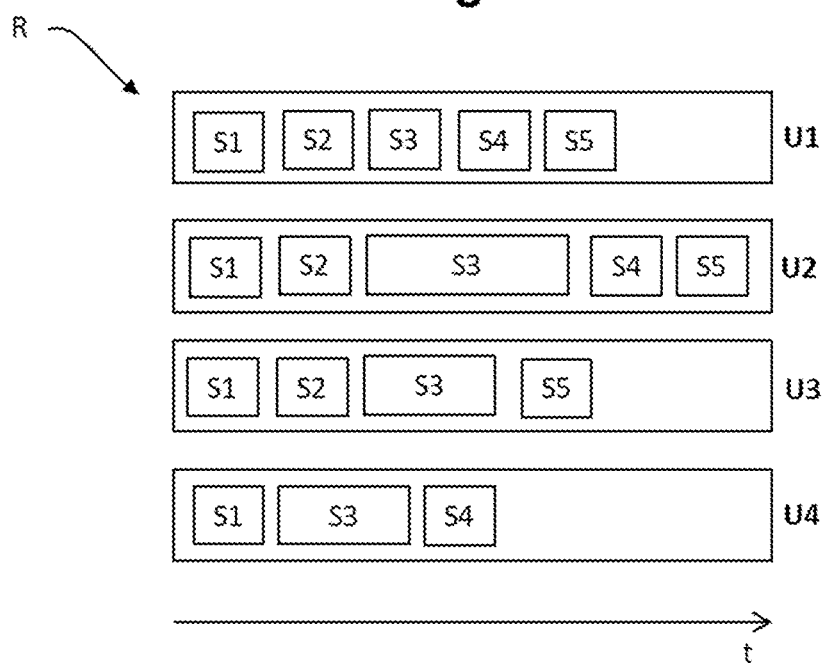

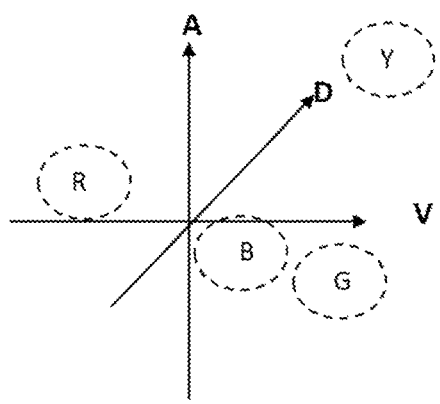
Fig. 6
Fig. 7
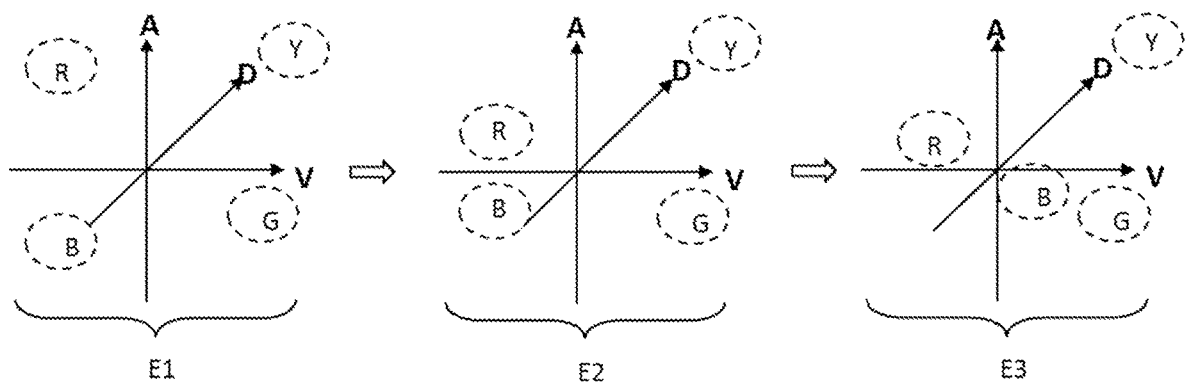

INTERACTIVE SYSTEM AND ASSOCIATED INTERACTION METHOD

The invention relates to an interactive system for interacting with at least one user occupying a motor vehicle. The invention also relates to a method for interaction with a user occupying a motor vehicle.

The transition to autonomous or semi-autonomous vehicles is exhibiting an increasing number of issues and challenges with regard to the creation of an intelligent and intuitive vehicle that makes it possible to make driving and/or travel more pleasant for the occupant, such as the driver or the passengers. In particular, some improvements may be focused on safety, comfort and entertainment or infotainment. In such autonomous or semi-autonomous vehicles, passengers and drivers tend to have more free time. There is an interest in making positive use of this free time in the vehicle.

Moreover, some examples of existing systems make it possible to evaluate the physiological or emotional state of an occupant of a motor vehicle. Indeed, it is known to perform measurements that make it possible to determine various parameters regarding an occupant, and thus to deduce therefrom a datum representative of his physiological or emotional state.

In general, the measurements may be performed using portable devices that make it possible to collect data such as skin conductivity, temperature, or even heart rate. The system that is used generally comprises a camera, for example a GoPro® camera.

In the known systems, the parameters that are obtained are then used to determine the emotional state of the occupant. One known model makes it possible to obtain, from the various parameters, a map of the emotional state of the passenger. This state may thus be represented by a point in a two-dimensional space formed by an abscissa axis corresponding to valence (intrinsically pleasant or unpleasant quality of a stimulus or a situation) and an ordinate axis corresponding to arousal (strength of the emotional stimulus).

The aim of the invention is to interact with the user on the basis of the detected physiological or emotional state, in order to improve his free time in the vehicle.

Another aim is to improve known systems by proposing an interactive system that makes it possible to model the physiological or emotional state of a user occupying a vehicle, and to interpret this state so as to integrate additional parameters into the model that is used.

To this end, one subject of the invention is an interactive system for interacting with at least one user occupying a motor vehicle comprising at least one interface configured so as to interact with the user, and an operating system configured so as to run an application selected by the user via the interface.

According to the invention, the interactive system comprises:
 a. a measuring device comprising at least one sensor configured so as to acquire at least one physiological parameter of the user, and
 b. an on-board processing unit configured so as to be connected to the interface and to the measuring device, such that the processing unit comprises:
  i. an interpretation module configured so as to receive the physiological parameter and to define, based on the physiological parameter, a datum representative of the physiological state of the user by way of an evaluation model for evaluating the physiological state of the user, and
  ii. an analysis module configured so as to compare data representative of the physiological state of the user before and during the execution of an application for managing a remedial exercise to be performed by the user to improve his physiological state, and to adjust at least one parameter of the remedial exercise, on the basis of the results of the comparison.

As a variant or in addition, the interpretation module of the processing unit may be configured so as to define, based on a predefined number of physiological parameters of the user, a datum representative of the emotional state of the user by way of an evaluation model for evaluating the emotional state of the user.

The remedial exercise is thus specifically adapted for the user, thereby making it possible to move toward an optimum physiological or emotional state when the user performs the remedial exercise.

The interactive system may furthermore comprise one or more of the following features, taken separately or in combination.

The one or more physiological parameters are for example vital signs.

The parameter of the remedial exercise may be adjusted during the current remedial exercise. As a variant or in addition, the parameter may be adjusted for a later session of the remedial exercise.

The measuring device comprises at least one sensor for capturing a parameter of the environment of the user in the motor vehicle.

At least one sensor of the measuring device may be configured so as to acquire at least one physiological parameter of the user before and after adjustment of the parameter of the remedial exercise.

The interpretation module may be configured so as to define, based on the physiological parameters, a datum representative of the physiological state of the user before and after adjustment of the parameter of the remedial exercise.

The analysis module may be configured so as to compare the data representative of the physiological state of the user before and after adjustment of the parameter of the remedial exercise. This makes it possible to improve the adjustment of the remedial exercise.

At least one sensor of the measuring device may be configured so as to acquire at least one physiological parameter of the user when the application is executed, during at least one sequence from among:
 a. a sequence of choosing from a menu of the application,
 b. a relaxation or preparation sequence, before the user performs the remedial exercise,
 c. a sequence of the user performing the remedial exercise,
 d. a sequence of explaining the remedial exercise,
 e. a sequence of feedback from the user about the remedial exercise performed.

The analysis module may be configured so as to adjust at least one parameter of at least one sequence, chosen from among the type of at least one sequence, the duration of at least one sequence, the intensity of at least one sequence, the speed of at least one sequence or the execution of at least one sequence.

According to one option, the explanation sequence is after the performance of the remedial exercise.

The selected application is advantageously an application for managing a remedial exercise to be performed by the user to improve his emotional state.

The datum representative of the emotional state of the user corresponds for example to a point in a characterization space characterizing the emotional state of the user.

According to one approach, the characterization space characterizing the emotional state of the user is a two-dimensional space, formed by a first axis corresponding to valence and a second axis corresponding to arousal.

According to another approach, the characterization space characterizing the emotional state of the user is a three-dimensional space. The three-dimensional characterization space characterizing the emotional state is formed by a first axis corresponding to valence, a second axis corresponding to arousal and a third axis corresponding to dominance.

According to another aspect, the interactive system may comprise at least one actuator configured so as to activate at least one multi-sensory stimulus in order to interact with the user during at least one sequence of the remedial exercise, said stimulus making it possible to modify the physiological and/or emotional state of the user. The multi-sensory environment is thus modified for a better perception of the exercise.

According to one option, the sensor is configured so as to capture a physiological parameter of the user before activation of said stimulus and when said stimulus interacts with the user. The interpretation module is configured so as to define, based on the captured physiological parameters, data representative of the physiological state of the user before activation of said stimulus and when said stimulus interacts with the user.

The measuring device may comprise at least one sensor configured so as to capture performance data from the user during a session of the remedial exercise when the application is executed.

The processing unit may comprise a performance study module for determining, based on the performance data, whether the user has performed the remedial exercise in accordance with the instructions of the application and/or for defining the progress of the user in comparison with at least one previous performance.

The processing unit may comprise a memory medium on which the performance data are intended to be recorded.

As a variant or in addition, the performance data may be downloaded onto a data storage medium, external to the motor vehicle, and be analyzed by a processing means external to the motor vehicle and/or be consulted by a medical or healthcare team.

The interactive system may comprise a telephony and/or messaging and/or video telecommunications module, so as to allow the user to interact with a team of specialists in the field of the downloaded application when the application is executed, for example during a sequence of performing the remedial exercise.

Said at least one sensor of the measuring device may be a sensor without contact with the user, chosen from among at least an ultra-wideband radar, an infrared camera, a sensor in the visible spectrum, a microphone.

The ultra-wideband radar has for example a frequency between 10 GHz and 1 THz, in particular between 50 GHz and 160 GHz.

The infrared camera may be configured so as to detect wavelengths between 0.7 μm and 100 μm, in particular between 25 μm and 100 μm.

The sensors of the measuring device are advantageously on board the motor vehicle.

The interface is on board the motor vehicle.

The interactive system may comprise a mobile terminal configured so as to be connected to the processing unit, the mobile terminal comprising the interface for interacting with the user.

The invention also relates to a method for interaction with at least one user occupying a motor vehicle, configured so as to be implemented at least partially by an interactive system as defined above.

The interaction method comprises the following phases:
a. a measuring phase of measuring at least one physiological parameter of the user by way of at least one sensor of the measuring device of the interactive system,
b. a reception and interpretation phase of receiving and interpreting the physiological parameter, performed by an interpretation module of the processing unit of the interactive system, in order to define, based on the physiological parameter, a datum representative of the physiological state of the user by way of an evaluation model for evaluating the physiological state of the user,
c. a remediation phase comprising executing an application for managing a remedial exercise to be performed by the user, and during which the user performs the remedial exercise of the application, and
d. an analysis phase, performed by an analysis module of the processing unit, in order to compare data representative of the physiological state of the user before and during the execution of the application, and in order to adjust at least one parameter of the remedial exercise on the basis of the comparison results.

The interaction method may furthermore comprise one or more of the following features, taken separately or in combination.

One or more phases are advantageously implemented continuously.

The measuring phase of measuring at least one physiological parameter of the user may be implemented before the execution of the application and also when the application is executed, during at least one sequence.

During the reception and interpretation phase, a datum representative of the emotional state of the user may be defined based on the physiological parameter of the user by way of an evaluation model for evaluating the emotional state of the user.

The datum representative of the emotional state of the user is placed in a characterization space characterizing the emotional state of the user, which is for example two-dimensional or three-dimensional.

According to one option, the characterization space characterizing the emotional state of the user, such as a three-dimensional or alternatively two-dimensional space, is adapted on the basis of additional data, in particular the culture and/or the education of the user and/or the personal life and experience of the user.

During the remediation phase, the application is executed in a predefined number of sequences from among:
a. a sequence of choosing from a menu of the application,
b. a relaxation or preparation sequence, before the user performs the remedial exercise,
c. a sequence of the user performing the remedial exercise,
d. a sequence of explaining the remedial exercise,
e. a sequence of feedback from the user about the remedial exercise performed.

The interaction method may comprise a performance study phase comprising: a step for capturing performance data from the user during a session of the remedial exercise, when the application is executed, and a step for determining, based on the captured performance data, whether the user has performed the remedial exercise in accordance with the instructions of the application and/or for defining the progress of the user.

The interaction method may comprise a step for transmitting the measurements to a memory medium internal to the vehicle or a storage medium external to the vehicle.

The interaction method may comprise a step of controlling an actuator in the motor vehicle so as to activate at least one multi-sensory stimulus in order to interact with the user during at least one sequence of the remedial exercise, said stimulus being designed to make it possible to modify the physiological and/or emotional state of the user, and a physiological parameter of the user is captured before the control step and when said stimulus interacts with the user, so as to define, based on the captured physiological parameters, data representative of the physiological state of the user before and during the control step.

The interaction method may also comprise a step for informing the user about his physiological or emotional state and/or about the stimulus applied.

Other features and advantages of the invention will become more clearly apparent on reading the following description, given by way of illustrative and non-limiting example, and the appended drawings, in which:

FIG. 1 schematically shows functional blocks of an interactive system for interacting with a user in a vehicle and of a remote server.

FIG. 4 schematically shows an axis of evolution of the emotional state of the user in the three-dimensional characterization space characterizing the emotional state.

FIG. 5 is a schematic depiction of successive sequences, adapted for respective users, of a remedial exercise.

Figure 2:
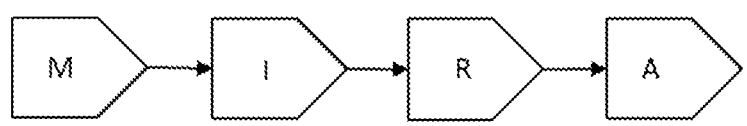
FIG. 2 is a schematic diagram of at least part of an interaction method implemented at least partially by the interactive system of FIG. 1.

FIG. 6 is a schematic depiction of a map for the sense of sight used in the method of FIG. 2.

FIG. 7 is a schematic depiction of the construction of the map from FIG. 6.

In these figures, identical elements bear the same references.

The following embodiments are examples. Although the description refers to one or more embodiments, this does not necessarily mean that each reference concerns the same embodiment, or that the features apply only to a single embodiment. Simple features of various embodiments may also be combined or interchanged to provide other embodiments.

In the description, some elements may be indexed, such as for example first element or second element. In this case, this is a simple indexing to differentiate between and name elements that are close but not identical. This indexing does not imply any priority of one element over another, and such names may easily be interchanged without departing from the scope of the present description. This indexing does not imply an order in time either.

Interactive System

Figure 1:
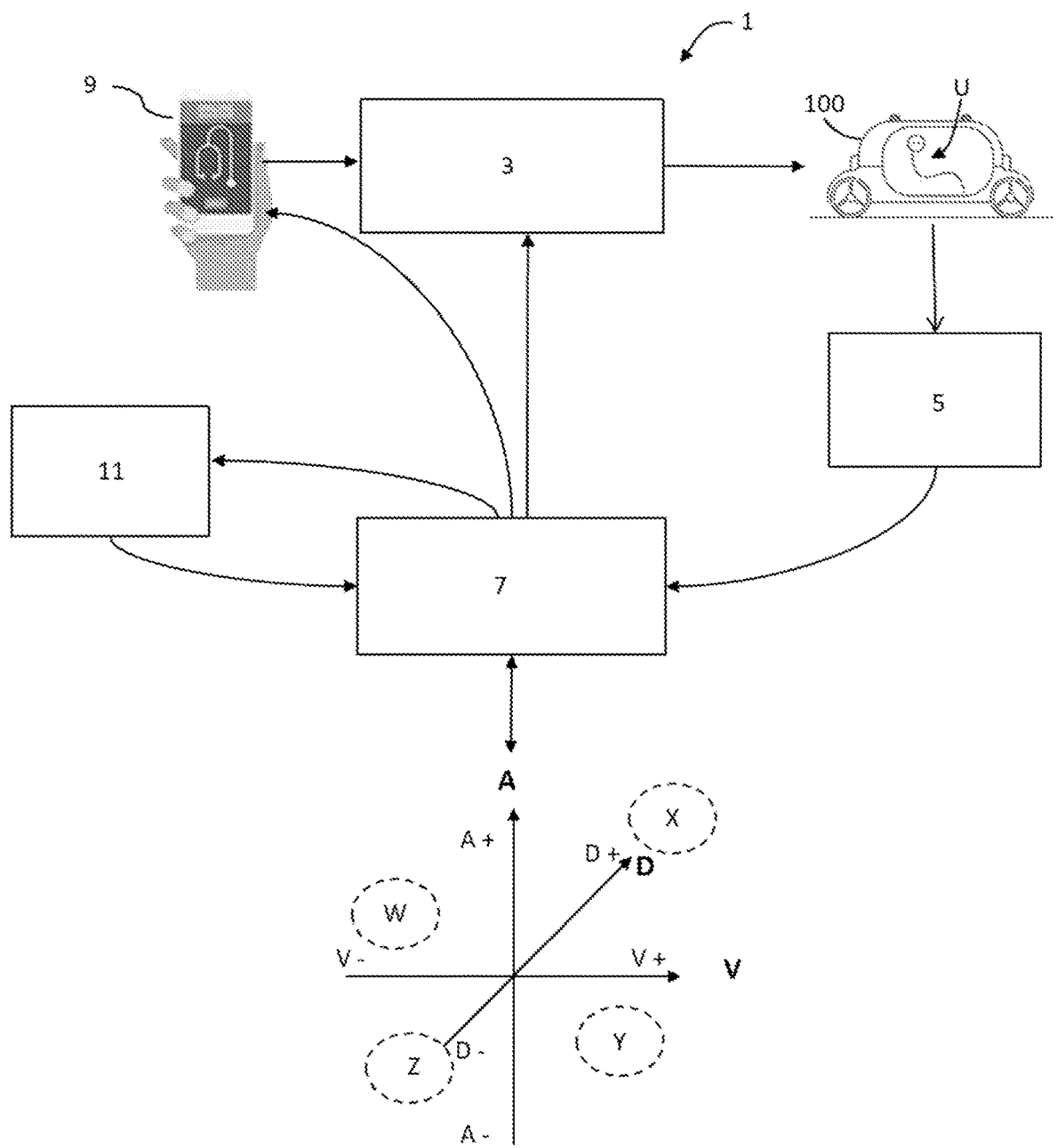

With reference to FIG. 1, the invention relates to an interactive system 1 for interacting with one or more users U occupying a motor vehicle 100, a driver and/or one or more passengers. Such an interactive system 1 makes it possible to at least partially implement a method for interaction with the user U, described in more detail below.

The interactive system 1 makes it possible to supervise one or more sessions of a remedial exercise that may be performed by a user U in the vehicle to improve his physiological or emotional state. In addition, the interactive system 1 may possibly act on the multi-sensory environment of the user U, so that said user has a better perception of the remedial exercise.

The remedial exercise may be a meditation exercise or a relaxation exercise. A leisure exercise in an area of interest of the user U could be contemplated.

As a variant, it may be an exercise in a primarily therapeutic setting. In particular, the therapeutic exercise may be an exercise with repetitive movements or repetitive actions that do not require the physical presence of a healthcare specialist, therapist, nurse or doctor. For example, without limitation, a therapeutic exercise may be chosen from among one of the following fields: speech therapy, optometry, orthoptics, rehabilitation, or even physiotherapy, concentration, breathing.

Advantageously, the interactive system 1 may be configured so as to automatically select and propose an application of a remedial exercise to the user U that corresponds to his physiological or emotional state. As an alternative or in addition, the interactive system 1 may be configured so as to specifically adapt the remedial exercise to the user.

To this end, the interactive system 1 comprises one or more interfaces 3 for interacting with a user U, a measuring device 5, and a processing unit 7 on board the motor vehicle 100, configured so as to be connected to the interface or to the interfaces 3 and to the measuring device 5.

The term "connected" is understood to mean a computer link between the processing unit 7 and the interface 3 or the interfaces 3, and the measuring device 5, so as to be able to exchange data. This may be a wired or wireless link. Data may for example be exchanged via a CAN ("Controller Area Network"), LIN BUS, Wi-Fi or Bluetooth network or the like.

The interface 3 may be on board the motor vehicle 100. Such an interface 3 is generally called a human-machine interface, known by the acronym HMI.

As a variant or in addition, the interactive system 1 may comprise a mobile terminal 9, such as a smartphone, and may be configured so as to be connected to the processing unit 7 of the motor vehicle 100. Such a mobile terminal may comprise an interface 3 for interacting with the user.

The interaction may take place through sound and/or through images and/or through tactile feedback.

Non-exhaustively, at least one command input interface and one output interface may be provided. The output interface may or may not be the command input interface.

In particular, the interactive system 1 may comprise at least one display interface 3. A display interface makes it possible for example to display a scrolling menu allowing the user to browse and make a choice from multiple options. The interactive system 1 may have one or more display interfaces 3 that may take the form for example of one or more wearable devices, such as a watch and/or glasses and/or a bracelet and/or a belt and/or a shirt.

A display interface 3 in the form of a screen, which may or may not be a touch screen, may also be provided. The touch screen makes it possible to act both as a command input interface through pressing or contact from the user U, and as an output interface through a display.

The interface 3, or at least one of the provided interfaces, makes it possible to receive one or more notifications for the attention of the user U, in particular regarding at least one application available on the server 11. One or more notifications may also make it possible to inform the user U about his physiological or emotional state, following an analysis of data obtained by the measuring device 5, as described in more detail below.

The measuring device 5 comprises one or more sensors configured so as to implement one or more measuring phases of the interaction method described below.

The sensors of the measuring device 5 are in particular configured so as to acquire at least one parameter linked to the user or multiple users. Such acquisition may take place at any time, in particular before, during or after the execution of an application, or even depending on whether or not the multi-sensory environment is modified.

The parameters linked to the user may comprise at least one physiological parameter of the user. Without being exhaustive or limiting, the physiological parameters may be vital signs, such as heart rate, pulse, breathing, or even the color of the skin on the face in order to detect a blood flow.

The sensors are preferably sensors on board the motor vehicle 100. The presence of the motor vehicle sensors in the vehicle may be linked to infotainment in the vehicle and to safety and comfort factors.

They may be sensors without contact with the user U, or even contact-based sensors.

The sensors may comprise one or more cameras, for example in the visible spectrum, vital sign sensors, one or more microphones.

At least one microphone may record the voice of the user U or users in the motor vehicle 100.

The sensors, in particular vital sign sensors, may for example take the form of contactless sensors, such as for example a radar, a camera. As an alternative or in addition, the sensors may be provided in wearable elements (watch, shirt, bracelet, etc.), worn by the user U.

One or more cameras may be provided in order to identify facial expressions or postures of the user U.

At least one camera may be a time-of-flight camera.

In one preferred embodiment, one or more cameras may in particular be infrared cameras configured so as to take images in the infrared spectrum. These cameras are for example directed at the expected positions of the various occupants of the vehicle: driver's seat, passenger seat, back seat, etc. In particular, one or more very wide-angle cameras (for example of the "fisheye" type) may cover multiple positions simultaneously. Infrared cameras preferentially detect wavelengths between 0.7 µm and 100 µm, preferentially 25 µm and 100 µm.

These cameras advantageously comprise near-infrared ("NIR") and/or far-infrared ("FIR") cameras.

The images from NIR, near-infrared, cameras may for example be used to define the position, dimensions and movements of various parts of the body of a user U of the vehicle. The images from FIR, far-infrared, cameras may for example be used to identify the parts of the body of the user U exchanging the most heat with the passenger compartment, for example the head and the hands, which are not covered by clothes and thus appear hotter.

According to one particular embodiment, the interactive system 1 comprises an ultra-wideband short-range radar. The frequency of the radar may for example be between 10 GHz and 1 THz, preferably between 50 GHz and 160 GHz.

Vital sign sensors in contact with the passenger may also be used. For example, they take the form of conductive elements installed in parts of the vehicle (armrest, steering wheel, seat, etc.). These vital sign sensors may be configured so as to measure parameters such as heart rate and/or pulse rate, respiratory rate and/or amplitude, skin conductivity, brain waves, etc.

As a variant or in addition, other types of parameters may also be retrieved by way of other sensors.

The measuring device 5 advantageously makes it possible to determine the environment of the one or more passengers, which may influence the physiological or emotional state of the one or more passengers. Data such as temperature, light intensity, noise, vehicle speed, etc. may thus be collected.

The measuring device 5 may also comprise biosensors able to detect parameters such as organic compounds, ions, bacteria or the like.

Furthermore, at least one sensor of the measuring device 5 may be configured so as to capture performance data from the user U during a session of the remedial exercise. This may involve, without limitation, tracking the evolution of the position and/or of the movements performed by the user, for example of his eyes, of a limb, of a part of the body, monitoring his breathing over a session or the like.

Moreover, the processing unit 7 may comprise one or more processing means configured so as to at least partially implement the interaction method described below.

In general, the processing means may comprise one or more of the means from among one or more telecommunications or telematics means, a comparator, at least one computer, a processor and/or any other hardware for executing or not executing software, an application-specific integrated circuit known by the acronym ASIC, a read-only memory known by the acronym ROM, a random access memory known by the acronym RAM, or other memory, or other conventional or customized hardware.

The modules of the processing unit 7 that are described below may comprise one or more of these processing means. In addition, the modules as defined below are distinguished between in order to better highlight their functionalities; of course, processing means may or may not be common between various modules of the processing unit 7.

By way of example, the processing unit 7 may comprise an interpretation module configured so as to receive one or more parameters linked to the user U from one or more sensors of the measuring device 5.

The interpretation module may be configured so as to define, based on the one or more parameters obtained by the measuring device 5, a datum representative of the physiological state of the user. To this end, the processing unit 7, in particular the interpretation module, is configured so as to use an evaluation model for evaluating the physiological state of the user U.

In particular, the processing unit 7, in particular the interpretation module, may be configured so as to define, based on a predefined number of parameters linked to the user, in particular physiological parameters, a datum representative of the emotional state of the user U using an evaluation model for evaluating the emotional state of the user U.

According to one exemplary embodiment, the datum representative of the emotional state corresponds to a point in a characterization space characterizing the emotional state of the user U. As shown schematically in FIG. 1, the characterization space characterizing the emotional state of the user U may be a three-dimensional space. This three-dimensional characterization space characterizing the emotional state is formed by a first axis corresponding to valence V, a second axis corresponding to arousal A and a third axis corresponding to dominance D.

As an alternative, the characterization space characterizing the emotional state of the user U could be a two-dimensional space formed by a first axis corresponding to valence and a second axis corresponding to arousal.

Valence V characterizes the level of pleasure (V+) or displeasure (V−) associated with an emotion. In other words, valence makes it possible to characterize how an individual experiences a situation, positively (V+), by being happy, or negatively (V−), by being sad, angry, unhappy.

Arousal A may be defined as the intensity of the response generated by a situation, an emotion. In other words, arousal makes it possible to define whether the individual experiences the situation with a great deal of excitement (A+), or on the contrary with little excitement, if he is relaxed, asleep, passive (A−).

Dominance D, for its part, characterizes the level of mastery and control of the individual's response to this emotion. In other words, dominance makes it possible to characterize whether the individual is in control, responsible for his reaction and his actions (D+) or on the contrary whether he is overwhelmed, impulsive, controlled by his emotions (D−).

One example of a map of the emotional state in the three-dimensional space A, V, D is shown in FIG. 1. In this example, W corresponds for example to a state of anxiety, X corresponds for example to a state of ecstasy, Y corresponds for example to a state of serenity, and Z corresponds for example to a state of depression. The point of intersection of the three axes of the three-dimensional space A, V, D corresponds to the neutral position of the emotional state of the user U.

The processing of the evaluation model for evaluating emotion may be improved. In particular, the map may be modified by taking into account the impact of the culture and/or the education of the occupant, making it possible to obtain a user profile for each user U. The map may also be adapted taking into account the impact of the personal life and/or the experience of the user U.

In addition, the processing unit 7 may comprise a data communication module for communicating data with a server 11 storing in particular a library of applications for managing remedial exercises, at least one datum representative of a physiological and/or emotional state being for example associated with each application. The applications in the library are intended to be downloaded on demand in the motor vehicle 100.

The processing unit 7 may comprise a data processing module configured so as to select, from among the applications in the library and on the basis of one or more data representative of the physiological and/or emotional state of the user U and the datum representative of a physiological and/or emotional state associated with each application, at least one application for managing a remedial exercise to be performed by the user U to improve his physiological and/or emotional state.

The processing unit 7 may comprise an information module configured so as to notify the user, via one or more interfaces 3, of at least one item of information regarding the one or more selected applications. The processing unit 7, for example the information module, may comprise one or more processing means for detecting a validation action from the user U via the interface 3, for example by pressing a touch screen, or by selecting the notified application via a control knob or a touchpad.

The interactive system 1 may host applications available on the server 11. To this end, the processing unit 7 may comprise a download module for downloading the application validated by the user U from the server 11. The interactive system 1 comprises an operating system that makes it possible to execute the application downloaded on demand from the server 11.

The processing unit 7 comprises at least one processing means for detecting a command to execute the application from the user U via the interface 3.

According to one advantageous option, the processing unit 7 may comprise an analysis module intended to analyze the physiological or emotional state of the user U when he performs the remedial exercise, and to deduce therefrom how to adapt this exercise specifically for the user, so that he is able to move toward an optimum state.

To this end, the analysis module is configured so as to compare data representative of the physiological state of the user that are obtained based on parameters linked to the user captured by the measuring device 5 before and during the execution of an application. The analysis module may, on the basis of the comparison results, determine whether an adjustment to the remedial exercise is necessary, and adjust at least one parameter of the remedial exercise.

The parameter to be adjusted may be chosen from among the type of at least one sequence, the duration of at least one sequence, the intensity of at least one sequence, the speed of at least one sequence or the execution or lack of execution of at least one sequence.

The processing unit 7 may furthermore comprise a performance study module configured so as to receive performance data obtained by the measuring device 5 during a session of the remedial exercise, and to evaluate the performance of the user U and/or his progress in comparison with at least one previous performance.

The processing unit 7 may comprise a memory medium intended to store one or more data, such as parameters linked to the user U, data representative of the physiological or emotional state of the user U, performance data. As a variant or in addition, one or more data may be intended to be downloaded onto a data storage medium, external to the motor vehicle 100, and intended to be analyzed by a processing means external to the motor vehicle 100 and/or to be consulted by a medical or healthcare team.

Furthermore, the interactive system 1 may comprise a telephony and/or messaging and/or video telecommunications module, so as to allow the user U to interact with a team of specialists in the field of the downloaded application when the application is executed, for example during a sequence of performing the remedial exercise. The telecommunications module may be on board the motor vehicle 100 or, as an alternative, be integrated into the mobile terminal 9.

Advantageously, the interaction with the user U may also take place using multi-sensory stimuli, in particular by way of equipment and physical elements in the motor vehicle 100, for example through massage and/or vibration and/or by adjusting at least one aeraulic parameter of an air flow intended to flow through the passenger compartment, such as the temperature and the flow rate, the temperature of an item of equipment or physical element in the vehicle such as the steering wheel or a seat, the surrounding odor, the lighting in the passenger compartment, or the sound environment.

To this end, the interactive system 1 may comprise at least one actuator configured so as to activate at least one multi-sensory stimulus in order to interact with the user U, so as to modify the physiological or emotional state of the user U.

The multi-sensory stimuli are for example based on the five senses: sight, smell, touch, hearing, taste. The multi-sensory stimuli that are used may for example be, for sight: the use of interior lighting with lights of various colors and/or of various intensities; for smell: the use of a nebulizer or a diffuser to diffuse perfume, essential oils or even pheromones; for touch: the use of radiant panels, water nebulization, the use of hot and/or cold jets of air; for hearing: the selection of sounds or music or background noises; for taste: the diffusion of perfume or nebulization able to create pheromones combining the five main flavors, specifically salty, sour, bitter, sweet, umami. Other types of stimuli may be considered.

At least one sensor of the measuring device 5 may be configured so as to capture a parameter linked to the user, for example before and during the application of a stimulus.

The interpretation module of the processing unit 7 may be configured so as to define, based on the captured parameters, the data representative of the physiological state of the user before activation of the stimulus and when the stimulus interacts with the user.

Interaction Method

With reference to FIGS. 1 and 2, the method for interaction with a user is described below. The following description refers to one user. Of course, the interaction method may be applied, simultaneously or not simultaneously, to multiple occupants of the motor vehicle.

The interaction method may be implemented at least partially by the interactive system as described above.

Selection of a Remedial Application

According to a first aspect, the interaction method makes it possible to choose and to propose an application of a remedial exercise to be performed by the user U on the basis of his physiological or emotional state.

To this end, the interaction method comprises a measuring phase M during which one or more parameters linked to the user U, in particular physiological parameters of the user U, are acquired. This measuring phase M may be performed by at least one sensor of the measuring device 5 of the interactive system 1 described above. The measurements may be performed simultaneously or one after the other for various users in the motor vehicle.

The measurement of at least one parameter linked to the user U may take place at any time, in particular before, during or after the execution of the application of a remedial exercise. The measurement may optionally also take place before, during or after the application of a stimulus.

Parameters describing the environment in which the user U is located may also be captured and collected so as to deduce therefrom their possible effect on the physiological or emotional state of the user U.

The measuring phase M of measuring at least one parameter linked to the user U may be implemented prior to the execution of the application and also when the application is executed.

The data obtained in the measuring phase M may be transmitted to the memory medium internal to the motor vehicle 100 or a storage medium external to the motor vehicle.

The interaction method may comprise a reception and interpretation phase I of receiving and interpreting the one or more parameters obtained in the measuring phase M. This reception and interpretation phase I may be performed by the processing unit 7 of the interactive system 1, in particular the interpretation module of this processing unit 7.

During the reception and interpretation phase I, a datum representative of the physiological state of the user U is defined based on the one or more received parameters, by way of the evaluation model for evaluating the physiological state of the user U. The physiological parameters are modeled so as to obtain a datum representative of the physiological state of the user, in particular of his emotional state. The representative datum may be represented in an characterization space characterizing the emotional state, such as a three-dimensional space, using the evaluation model for evaluating emotions.

Figure 3:
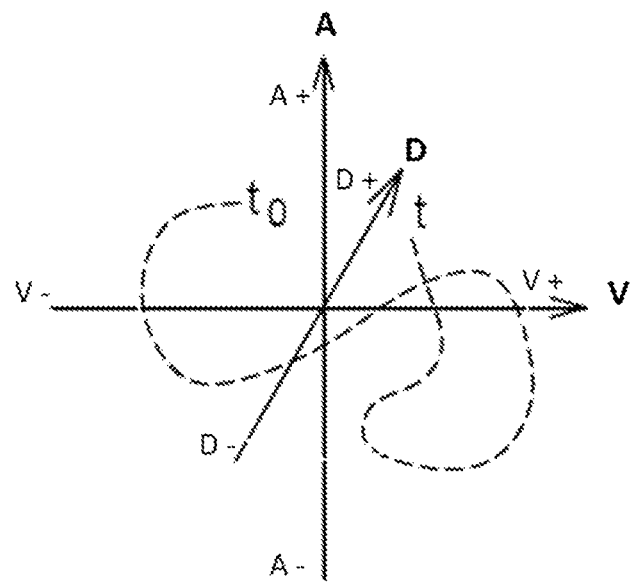
FIG. 3 is a schematic depiction of a map of the emotional state of a user in a three-dimensional characterization space characterizing the emotional state.

FIG. 3 illustrates one example of the placement of the representative datum, described above and obtained through the processing unit 7, in the characterization space, such as the three-dimensional space A, V, D. This datum varies over the course of the time spent by the user U in the motor vehicle 100. Thus, a first representative datum is provided at a time $t_0$, and the representative datum provided at a time t corresponds to the present. Continuous measurements are preferably performed, so as to obtain the curve shown in FIG. 3. However, discrete measurements may also be performed.

Once the representative datum has been evaluated, an analysis or processing step may be performed, so as to determine the physiological or emotional state of the user U, for example on the basis of the placement of the representative datum in the characterization space, such as the three-dimensional space A, V, D. This analysis step makes it possible to map the physiological or emotional state of the user U and decide whether or not an action is necessary to improve the state of the user U.

With reference again to FIG. 1, if an action is necessary, the interaction method may comprise a selection phase of selecting at least one application from the library stored on the server 11. These are in particular applications for managing remedial exercises to be performed by the user U to improve his physiological or emotional state, on the basis of the defined datum representative of the physiological or emotional state of the user U. The choice of application depends on the desired remediation.

To this end, the interaction method may comprise a step of interrogating the server 11 to identify suitable applications in the library for remedying the physiological or emotional state of the user U. This may be implemented by the processing unit 7, in particular the data communication module of the processing unit 7 for communicating data with the server 11.

The process of selecting the application takes place on the basis of the physiological/emotional state of the user U as measured by the measuring device 5 in the motor vehicle 100.

For example, if the physiological state of the user U corresponds to a stressed or nervous state, and/or if his emotional state corresponds to a state of rage or anger, a relaxation application may be selected. Or else, if the physiological state of the user U corresponds to a state of nervousness and/or if his emotional state corresponds to a state of fear, a meditation application may be selected. On the contrary, if the user demonstrates a calm physiological state and/or a neutral emotional state, an application of multiple choice exercises for example may be selected. According to another example, if the user is in a calm physiological state and/or in an emotional state of the order of disgust, a learning application may be proposed to him; for example, in the event of a vision anomaly, an orthoptic application may be selected for an eye movement exercise or the like. Or else, if the user is in a calm physiological state and/or in an emotional state corresponding to joy, an application of a rehabilitation exercise may be selected. According to another example, if the physiological state corresponds to a drowsy state and/or if the emotional state corresponds to sadness, an application of a stimulation exercise may be selected. If the physiological state of the user U demonstrates fatigue and/or if the emotional state corresponds to a state of surprise, an application of a concentration exercise may be selected. According to yet another example, if a state of inattentiveness is detected, an application of attention exercises may be selected.

This selection may be made by a data processing module of the processing unit 7 of the interactive system 1.

To this end, the map of the physiological or emotional state of the user U may be correlated with one or more maps corresponding to various applications stored on the server 11. Among the various applications of remedial exercises available in the library, those that make it possible to return the state of the user U to a neutral position may be selected. For example, in the case of a characterization space characterizing the emotional state of the user, such as a three-dimensional space A, V, D or, as a variant, a two-dimensional space A, V, the one or more applications for which a representative datum is located symmetrically to the datum representative of the emotional state of the user about the neutral position in the characterization space, which may be three-dimensional A, V, D, may be selected, as shown schematically in FIG. 4. In this example, purely by way of explanation, the datum representative of the emotional state of the user at a given time is for example located at position P1 in the characterization space, which may be three-dimensional A, V, D. An application for which a representative datum is located in a position P2 symmetrical to the position P1 about the neutral position at the intersection of the axes A, V, D (or A, V in the case of a two-dimensional space) will tend to return the emotional state of the user to this neutral position, and will therefore be selected. The map of the applications may either be on the server 11 or be downloaded via the interactive system 1, for example to a storage space, provided for this purpose, of the processing unit 7.

With reference again to FIGS. 1 and 2, after this selection of one or more applications, the interaction method comprises a phase of notifying the user. This notification phase makes it possible to inform the user, via the interface 3 or one of the interfaces of the interactive system 1, with regard to the one or more applications that are selected automatically. At least one item of information regarding a selected application may be notified to the user U, for example through a display. This notification may be carried out by the processing unit 7 of the interactive system 1, for example the information module of the processing unit 7.

The notification may also make it possible to inform the user U about his physiological or emotional state.

The user U may then validate the application that is notified to him or one of the applications if a possibly classified list is notified to him. This validation may take place through interaction with the interface 3, for example by pressing on a touch screen on board or not on board the motor vehicle 100.

The interaction method may comprise a step of detecting a validation action from the user. This detection may be carried out by the processing unit 7, for example an information module of the processing unit 7.

This is followed by a download phase of downloading the application validated by the user U from the server 11, for example performed by a download module of the processing unit 7. The validated application is downloaded to a storage space, provided for this purpose, of the processing unit 7.

The interaction method also comprises a remediation phase R (FIG. 2).

This remediation phase R comprises executing the downloaded application. The user may then perform at least one session of the remedial exercise.

With reference to FIGS. 2 and 5, advantageously, the application takes place in a predefined number of sequences from among a sequence S1 of choosing from a menu of the application, a relaxation or preparation sequence S2, a sequence S3 of the user performing the remedial exercise, a sequence S4 of explaining the remedial exercise, a sequence S5 of feedback from the user about the remedial exercise performed. Preferably, the remedial exercise applications in the library are similarly sequenced. These various sequences S1 to S5 make it possible to accompany the user during the execution of the application.

The relaxation or preparation sequence S2 is prior to the sequence S3 of the user performing the remedial exercise. Indeed, by relaxing the user before performing the exercise, said user is able to perform the exercise effectively. Such a relaxation or preparation sequence S2 may have a relative duration, since it depends on the physiological or emotional state of the user. Indeed, there is no point in dragging out this relaxation or preparation sequence S2 if the user is already in a relaxed state, for example.

The sequence S4 of explaining the remedial exercise may be executed after the sequence S3 of performing the exercise. This sequence S4 makes it possible to explain the usefulness, the purpose of the exercise, its importance and/or its therapeutic effect to the user. During this explanation sequence S4, the user may receive at least one item of information regarding his performance, and/or his progress. The user may also receive at least one item of information regarding his physiological or emotional state during the exercise.

According to one advantageous option, when the application is executed, the user may interact with at least one specialist or a team of specialists in the field in question, depending on the downloaded application. This interaction between the user and the team may take place via the telephony and/or messaging and/or video telecommunications module. The user may for example ask questions, verbally or in writing, during a sequence S3 of performing the remedial exercise, or during an explanation sequence S4, and receive a response from this team of specialists, or else during a feedback sequence S5. Like the user, the connected team may respond in writing or verbally.

The information entered by the user during the last feedback sequence S5 may be stored on the memory medium internal to the vehicle and/or on a storage medium external to the vehicle. This feedback information may be analyzed by at least one processing means of the interactive system 1 to improve the remedial exercise.

At least some of these sequences are essential, in particular the sequence S3 of the user performing the remedial exercise, and the sequence S1 of choosing from a menu of the application.

Other sequences S2, S4, S5 may be optional. In particular, one or more of the relaxation sequence S2, explanation sequence S4 and feedback sequence S5 may be omitted upon demand from the user via the interface 3. As a variant, some sequences S2, S4, S5 might not be proposed to the user automatically by the interactive system 1.

In addition, the sequences S1 to S5 may be adapted specifically for the user. The sequences may be adapted on the basis of the physiological or emotional state of the user during these sequences S1-S5, as detailed below.

The measuring phase M described above may take place during at least one of the sequences S1 to S5 when the application is executed.

In order to allow a personalized analysis of the performance of the user when he performs the remedial exercise, the interaction method may comprise a performance study phase. This performance study phase is in particular implemented during a sequence S3 of the user performing the remedial exercise.

The performance study phase comprises a step for capturing performance data from the user during a session of the remedial exercise, when the application is executed.

This is followed by a step for determining, based on the captured performance data, whether the user has performed the remedial exercise in accordance with the instructions of the application. The performance data may be compared to statistical or optimum data that may for example be accessible from the server 11 or be downloaded via the interactive system 1. Such statistical or optimal data are generally available when there is monitoring by a practitioner.

The performance study may be performed by the processing unit, and in particular by the performance study module of the processing unit.

As a variant or in addition, the interaction method may comprise a step for defining the progress of the user in comparison with at least one previous performance. To this end, the method may comprise one or more steps of comparing the data captured during various performances to produce progress statistics. In particular, it is possible to identify one or more aspects of the remedial exercise for which the user's performance shows an improvement, such as better concentration during the meditation exercise, or a more precise movement of a body part, or the like.

A notification phase may make it possible to inform the user of this progress.

Adaptation of the Exercise

According to a second aspect, the interaction method makes it possible to adapt a remedial exercise chosen by the user U and/or proposed automatically by the interactive system 1 of FIG. 1, on the basis of the physiological or emotional state of the user U. This second aspect comes as a variant or in addition to the first aspect of the interaction method described above.

According to this second aspect, in addition to the measuring phase M, reception and interpretation phase I and remediation phase R described above with reference to FIGS. 1 to 5, the interaction method comprises an analysis phase A. This analysis phase A may be implemented by the processing unit 7 of the interactive system 1, in particular by the analysis module of the processing unit 7.

The analysis phase A makes it possible to potentially adjust the remedial exercise on the basis of the physiological or emotional state of the user U when he performs this exercise.

To this end, the analysis phase A may comprise a step for comparing data representative of the physiological state of the user that are defined based on parameters obtained by the measuring device 5 before and during the execution of the application. The analysis phase A comprises a step for determining, on the basis of the comparison results, whether an adjustment to the remedial exercise is necessary, and for potentially adjusting at least one parameter of the remedial exercise.

The analysis phase A may also take into account the performance data obtained by the measuring device 5, in order to potentially adjust the remedial exercise on the basis of the previous and/or current performance of the user, or on the basis of his progress.

As an alternative or in addition, the analysis phase A may also take into account data linked to the use of the motor vehicle, such as for example navigation data.

The parameter may be adjusted during the current remedial exercise. As a variant or in addition, the parameter may be adjusted for a later session of the remedial exercise.

Before the start of the exercise, for example at the start of the sequence S2 or S3, an analysis of the performance of a previous session and an adaptation on the basis of this performance analysis may take place.

The remedial exercise is adjusted by acting on the duration, the intensity, the type of content and the speed of a sequence S1, S2, S3, S4, S5 on the basis of the physiological state of the user during the sequences S1, S2, S3, S4, S5. For example, one or more sequences may have a shortened duration, or be sped up or slowed down for example. A change in the type of sequence may be for example to change the music if the exercise is accompanied by music and the previous music has the effect for example of making the user tense.

Also, depending on the physiological and/or emotional state of the user, at least one of the sequences, when it is not essential, might not be executed or deployed. The choice of the sequences to be executed is therefore adjusted. For example, if the interactive system 1, in particular the processing unit 7, determines that the user U is tired, one or more of the optional sequences, such as the relaxation sequence S2, explanation sequence S4, or feedback sequence S5, might not be executed.

In particular, if valence is excessively negative, the duration of one or more sequences may be reduced. On the contrary, if valence is more positive, the duration of one or more sequences may be increased. Similarly, if arousal is very positive, the duration of one or more sequences may be increased or even the intensity or the difficulty of one or more sequences may be increased. In the opposite case, if arousal is very negative, the duration of one or more sequences and/or the intensity may be significantly reduced.

For example, if the physiological state of the user is in an area corresponding to a drowsy state and/or if his emotional state reflects a state of rage or anger, the duration of one or more sequences may be reduced and the rate of these sequences may be adapted. For a stressed physiological state and/or a neutral emotional state, the duration may be stable and the rate adapted. If the physiological state of the user corresponds to nervousness and/or if his emotional state corresponds to fear, the rate of the sequences may be reduced and the explanation sequence may be longer. According to another example, if the physiological state of the user is in an area corresponding to a state of fatigue and/or if his emotional state is in an area corresponding to a state of disgust, the duration of one or more sequences may be reduced. On the contrary, if his physiological state corresponds to a calm state and/or if his emotional state reflects joy or sadness, the duration of one or more sequences may be extended. According to yet another example, if his physiological state corresponds to a calm state and/or if his emotional state corresponds to a state of surprise, the duration of one or more sequences may be extended and the rate of these sequences may be adapted.

To facilitate the understanding of the adjustment to the sequences S1-S5, four examples, chosen arbitrarily, are shown in FIG. 5. Each example corresponds to an adjustment to the remedial exercise for a respective user U1, U2, U3, U4.

Thus, for the first example, regarding the user U1, it is noted that the duration is shorter for example than for the user U2 in the second example. The total duration of all of the sequences S1 to S5 may be shortened by the interactive system 1, more precisely by the processing unit, for example after having determined, on the basis of the parameters obtained by the measuring device, that the user U1 is tired. This shortened duration may also be a consequence of a very good previous performance of the user U1, or else because the interactive system 1 has detected that the user U1 is on a short journey, for example based on navigation data collected in a known manner.

In the second example, regarding the user U2, the sequence S3 of performing the remedial exercise may have a longer duration in comparison with the other sequences S1, S2, S4, S5. The duration of the sequence S3 of performing the remedial exercise may be extended by the processing unit, for example after having determined, on the basis of the parameters obtained by the measuring device, that the user U2 has a need for deeper remediation, for example for a therapeutic exercise, or else if the processing unit determines that the user U2 is in a state of great concentration or alertness.

In the third example, regarding the user U3, the explanation sequence S4 is omitted. This omission may be implemented for example if the processing unit determines, on the basis of the parameters obtained by the measuring device, that the user U3 is tired, and/or that he has already performed this exercise and knows the explanation for it.

In the fourth example, regarding the user U4, the relaxation sequence S2 and feedback sequence S5. The relaxation sequence S2 may for example be omitted if the processing unit determines, on the basis of the parameters obtained by the measuring device, that the user U4 is already in a relaxed state, relaxed enough to perform the remedial exercise, and does not need any further relaxation. The feedback sequence S5 may for example be omitted if the processing unit determines, on the basis of the parameters obtained by the measuring device during a previous session, that the emotional state of the user U4 is more negative in this sequence S5, for example if valence becomes negative, or if it is of no benefit in this sequence S5.

Also, on the basis of the physiological or emotional state of the user, the interactive system may determine that the exercise chosen by the user is not relevant, for example because the user is not fit enough to perform it, and automatically propose stopping the exercise or performing another exercise more suited to the physiological or emotional state of the user. The interactive system then proposes a more appropriate alternative exercise, or may also propose to postpone the remediation until later.

The interactive system may also check, using the parameters obtained by the measuring device, whether the user reaches the expected level of relaxation during the performance of the relaxation sequence S2. If this level of relaxation is not reached, the interactive system may automatically propose not to perform the exercise (sequence S3). Indeed, in such a case, the exercise risks being irrelevant for obtaining the desired remedial effect.

In addition, the interaction method advantageously makes it possible to identify whether or not the adjustments made to the sequences are beneficial for the user.

To this end, the measuring phase M may be implemented before and after adjustment to the one or more parameters of the remedial exercise by at least one sensor of the measuring device 5 (see FIGS. 1 and 2). During the reception and interpretation phase I, a datum representative of the physiological or emotional state of the user U is defined for the periods before and after the adjustment to the one or more parameters of the remedial exercise.

During the analysis phase A, the data representative of the physiological or emotional state of the user U before and after adjustment to the parameter of the remedial exercise may be compared. On the basis of the comparison results, the analysis module may determine whether the adjustment to the one or more parameters has had a beneficial or, on the contrary, negative effect on the physiological or emotional state, for example by positioning the representative data in the three-dimensional space A, V, D, as described above. The interaction method thus does not target one-off remediation, but seeks to move, at all times, toward an optimum physiological and emotional state of the user U so that the remedial exercise takes place correctly. This optimum state may vary over time.

Adaptation of the Multi-Sensory Environment

According to yet another aspect of the interaction method, the multi-sensory environment of the user U may be adapted on the basis of his physiological or emotional state. This action on the multi-sensory environment may complement the remedial exercise. This makes it possible to offer the user U a better perception of the remedial exercise.

To this end, the map of the physiological or emotional state of the user U may be correlated with one or more maps corresponding to various stimuli, based on one or more of the five senses. By way of illustrative example, one example of a map corresponding to the sense of sight is shown schematically in FIG. 6.

The senses may be mapped in multiple steps E1, E2, E3, as illustrated in FIG. 7. For greater clarity, the map of a single sense, such as sight, is shown in FIG. 7. The initial map, in step E1, corresponds to a primary emotional state of the user, that is to say an emotional state in which the user reacts in a primary manner. The map is then modified taking into account the impact of the culture and/or the education of the user; this is step E2. It will be noted that, in the arbitrary example of FIG. 7, the colors red R and blue B are closer to neutrality along the axis A of arousal, in comparison with the initial map (E1). The last step E3 in the construction of the map concerns the impact of the personal life and/or the experience of the user. It will be noted that, in the arbitrary example of FIG. 7, the color blue B moves closer to the positive side along the axis of valence V and dominance D.

The interaction method, and in particular the remediation phase R, may comprise an action step in which at least one multi-sensory stimulus is applied so as to modify the physiological or emotional state of the user U (FIGS. 1 and 2). The choice of the stimulus or stimuli depends on the desired effect. After having placed the datum representative of the emotional state of the user U on the map, various types of actions may be selected.

For example, a stimulus located symmetrically about the neutral position in the characterization space characterizing the emotional state of the user U, such as the three-dimensional space A, V, D, may be applied. The emotional state of the user may thereby move toward the neutral position.

It is also possible to contemplate applying a stimulus positioned in the direction opposite the neutral position in the characterization space characterizing the emotional state of the user U, such as the three-dimensional space A, V, D (with respect to the initial position); so as to amplify an emotion, for example.

Provision may also be made to apply a stimulus that makes it possible to change from the initial position (initial status of the emotional state) to a given specific position (desired status of the emotional state), the one or more stimuli being chosen on the basis of the given specific position.

More specifically, the action step for applying a stimulus is a step of controlling at least one actuator in the motor vehicle so as to activate the multi-sensory stimulus. This stimulus may be applied during at least one sequence of the remedial exercise.

The method may comprise an information step in which the user is informed of the one or more stimuli applied.

With a view to always being better suited to the user U, the measuring phase M of measuring at least one parameter linked to the user may be implemented before the action step and when the stimulus interacts with the user U by at least one sensor of the measuring device 5. Based on these parameters, data representative of the physiological state of the user before and during the action step may be defined in the interpretation phase I, for example by the interpretation module of the processing unit 7.

During the analysis phase A, the data representative of the physiological or emotional state of the user U before and after application of the stimulus may be compared. On the basis of the comparison results, the analysis module may determine whether the application of the stimulus has had a beneficial or, on the contrary, negative effect on the physiological or emotional state, for example by positioning the representative data in the three-dimensional space A, V, D, as described above.

One or more phases of the interaction method according to one or the other of the aspects described above, in particular from among the measuring phase M, interpretation phase I, remediation phase R, and analysis phase A, may be implemented continuously. In addition, these phases M, I, R, A that are implemented continuously are also implemented in parallel with the execution of one or more of the sequences S1 to S5 as described above.

It will therefore be understood that the interaction method implemented at least partially by the interactive system 1 as described above may make it possible to automatically propose one or more applications in a library stored on a remote server 11. These applications relate to remedial exercises that correspond to the physiological or emotional state of the user U, defined based on measurements performed in the motor vehicle 100 and by interpreting these measurements using an evaluation model for evaluating the physiological or emotional state of the user U.

The interactive system 1 also makes it possible to manage, supervise remedial exercises performed in various sequences S1 to S5, and to adapt the sequences S1-S5 on the basis of the physiological or emotional state of the user U during the remedial exercises. The remedial exercise is thus specifically adapted for the user U, thereby making it possible to move toward an optimum physiological (or emotional) state when the user performs the remedial exercise.

Finally, the multi-sensory environment of the user U may be improved by applying one or more stimuli in order to promote a better perception of the remedial exercises by the user U.

The invention claimed is:

1. An interactive system for interacting with at least one user occupying a motor vehicle comprising:
   at least one interface configured so as to interact with the user;
   an operating system configured so as to run an application selected by the user via the interface;
   a measuring device comprising at least one sensor configured so as to acquire at least one physiological parameter of the user; and
   an on-board processing unit configured so as to be connected to the interface and to the measuring device, wherein the processing unit comprises:
      an interpretation module configured so as to receive the physiological parameter and to define, based on the physiological parameter, a datum representative of the physiological state of the user by way of an evaluation model for evaluating the physiological state of the user, and
      an analysis module configured so as to compare data representative of the physiological state of the user before and during the execution of an application for managing a remedial exercise to be performed by the user to improve his physiological state, and to adjust at least one parameter of the remedial exercise, on the basis of the results of the comparison,
   wherein at least one sensor of the measuring device is configured to acquire the at least one physiological parameter of the user when the application is executed, during at least one sequence from among:
      a sequence of choosing from a menu of the application,
      a relaxation or preparation sequence, before the user performs the remedial exercise,
      a sequence of the user performing the remedial exercise,
      a sequence of explaining the remedial exercise, and
      a sequence of feedback from the user about the remedial exercise performed, and
   wherein the analysis module is configured to adjust at least one parameter of the at least one sequence, the parameter being chosen from among a type, a duration, an intensity, a speed and an execution of the at least one sequence.

2. The interactive system as claimed in claim 1, wherein:
   at least one sensor of the measuring device is configured so as to acquire at least one physiological parameter of the user before and after adjustment of the parameter of the remedial exercise,
   the interpretation module is configured so as to define, based on the physiological parameters, a datum representative of the physiological state of the user before and after adjustment of the parameter of the remedial exercise, and
   the analysis module is configured so as to compare the data representative of the physiological state of the user before and after adjustment of the parameter of the remedial exercise.

3. The interactive system as claimed in claim 1, wherein:
   the interpretation module of the processing unit is configured so as to define, based on a predefined number of physiological parameters of the user, a datum representative of the emotional state of the user by way of an evaluation model for evaluating the emotional state of the user, the representative datum corresponding to a point in a characterization space characterizing the emotional state of the user, and the selected application is an application for managing a remedial exercise to be performed by the user to improve his emotional state.

4. The interactive system as claimed in claim 1, further comprising at least one actuator configured so as to activate at least one multi-sensory stimulus in order to interact with the user during at least one sequence of the remedial exercise, said stimulus making it possible to modify the physiological state of the user.

5. The interactive system as claimed in claim 1, wherein:
the measuring device comprises at least one sensor configured so as to capture performance data from the user during a session of the remedial exercise when the application is executed, and
the processing unit comprises a performance study module for determining, based on the performance data, whether the user has performed the remedial exercise in accordance with the instructions of the application and/or for defining the progress of the user in comparison with at least one previous performance.

6. The interactive system as claimed in claim 1, wherein said at least one sensor of the measuring device is a sensor without contact with the user, chosen from among at least an ultra-wideband radar, an infrared camera, a sensor in the visible spectrum, a microphone.

7. A method for interaction with at least one user occupying a motor vehicle, configured so as to be implemented at least partially by an interactive system as claimed in claim 1, the interaction method comprising:
a measuring phase of measuring at least one physiological parameter of the user by way of at least one sensor of the measuring device of the interactive system,
a reception and interpretation phase of receiving and interpreting the physiological parameter, performed by an interpretation module of the processing unit of the interactive system, in order to define, based on the physiological parameter, a datum representative of the physiological state of the user by way of an evaluation model for evaluating the physiological state of the user,
a remediation phase comprising executing an application for managing a remedial exercise to be performed by the user, and during which the user performs the remedial exercise of the application, and
an analysis phase, performed by an analysis module of the processing unit, in order to compare data representative of the physiological state of the user before and during the execution of the application, and in order to adjust at least one parameter of the remedial exercise on the basis of the comparison results.

8. The interaction method as claimed in claim 7, wherein, during the remediation phase, the application is executed in a predefined number of sequences from among:
a sequence of choosing from a menu of the application,
a relaxation or preparation sequence, before the user performs the remedial exercise,
a sequence of the user performing the remedial exercise,
a sequence of explaining the remedial exercise, and
a sequence of feedback from the user about the remedial exercise performed.

9. The interaction method as claimed in claim 7, further comprising controlling an actuator in the motor vehicle so as to activate at least one multi-sensory stimulus in order to interact with the user during at least one sequence of the remedial exercise, said stimulus being configured to make it possible to modify the physiological state of the user, and wherein a physiological parameter of the user is captured before the control step and when said stimulus interacts with the user, so as to define, based on the captured physiological parameters, data representative of the physiological state of the user before and during the control step.

* * * * *